(12) United States Patent
Drake et al.

(10) Patent No.: US 8,134,715 B2
(45) Date of Patent: Mar. 13, 2012

(54) ADJUSTABLE INTERFEROMETER FOR LASER ULTRASONIC MEASUREMENT

(75) Inventors: Thomas E. Drake, Fort Worth, TX (US);
Marc Dubois, Keller, TX (US)

(73) Assignee: iPhoton Solutions, LLC, Fort Worth, TX (US)

( * ) Notice: Subject to any disclaimer, the term of this patent is extended or adjusted under 35 U.S.C. 154(b) by 393 days.

(21) Appl. No.: 12/468,165

(22) Filed: May 19, 2009

(65) Prior Publication Data
US 2009/0290166 A1    Nov. 26, 2009

Related U.S. Application Data

(60) Provisional application No. 61/054,803, filed on May 20, 2008.

(51) Int. Cl.
| | |
|---|---|
| G01B 11/02 | (2006.01) |
| G01B 9/02 | (2006.01) |
| G01D 5/32 | (2006.01) |
| G01H 1/00 | (2006.01) |
| G01H 9/00 | (2006.01) |
| G01N 9/18 | (2006.01) |

(52) U.S. Cl. ............................ 356/502; 356/519; 73/655
(58) Field of Classification Search ............ 73/655–657; 356/454, 480, 502, 506, 519
See application file for complete search history.

(56) References Cited

U.S. PATENT DOCUMENTS

| | | | | |
|---|---|---|---|---|
| 5,080,491 A | * | 1/1992 | Monchalin et al. | 356/493 |
| 5,585,921 A | * | 12/1996 | Pepper et al. | 356/487 |
| 6,181,431 B1 | * | 1/2001 | Siu | 356/502 |
| 6,633,384 B1 | * | 10/2003 | Drake et al. | 356/432 |
| 6,637,266 B1 | | 10/2003 | Froom | |
| 6,819,432 B2 | * | 11/2004 | Pepper et al. | 356/498 |
| 7,474,411 B2 | * | 1/2009 | Dubois et al. | 356/502 |
| 7,864,338 B2 | * | 1/2011 | Pouet | 356/502 |
| 2002/0186380 A1 | | 12/2002 | Drake, Jr. | |
| 2004/0027578 A1 | * | 2/2004 | Drake et al. | 356/502 |
| 2005/0120803 A1 | | 6/2005 | Sokol et al. | |
| 2008/0007717 A1 | * | 1/2008 | Nielsen et al. | 356/73 |
| 2009/0262359 A1 | * | 10/2009 | Bajraszewski et al. | 356/454 |
| 2009/0290166 A1 | * | 11/2009 | Drake et al. | 356/491 |
| 2010/0134803 A1 | * | 6/2010 | Baier et al. | 356/498 |
| 2011/0110388 A1 | * | 5/2011 | Baroni et al. | 372/26 |

* cited by examiner

*Primary Examiner* — Patrick J Connolly
(74) *Attorney, Agent, or Firm* — Paul V. Storm; Mark D. Perdue; Storm LLP

(57) ABSTRACT

An interferometer includes a cavity including a pair of mirrors defining a cavity length. An input beam and a counter-propagating reference beam are directed into the cavity. The interferometer generates a feedback control signal and an ultrasound signal for optimal performance and measurement of a target, respectively.

37 Claims, 3 Drawing Sheets

ADJUSTABLE INTERFEROMETER FOR LASER ULTRASONIC MEASUREMENT

CROSS-REFERENCE TO RELATED APPLICATIONS

Pursuant to 35 U.S.C. §119(e), this application claims priority from, and hereby incorporates by reference for all purposes, U.S. Provisional Patent Application Ser. No. 61/054,803, entitled INTERFEROMETER FOR THE OPTICAL DETECTION OF ULTRASOUND, and filed May 20, 2008.

FIELD OF THE INVENTION

The invention generally relates to laser ultrasonic measurement, and more particularly to an adjustable interferometer for laser ultrasonic measurement.

BACKGROUND OF THE INVENTION

Laser ultrasonic measurement systems are frequently used for testing of various components and complex structures. These systems offer advantages over non-laser type systems (e.g., piezoelectric transducer-based systems). Laser ultrasonic systems are typically non-contact systems that test a structure by measuring ultrasonic waves induced in a structure. Typically, a short laser pulse is directed to a structure causing thermal expansion of the structure, which generates ultrasonic waves. Laser ultrasonic systems are well suited for many industrial applications such as measurement of steel at high temperature, measurement of paint thickness, and non-destructive testing of complex composite structures.

One drawback of existing confocal Fabry-Perot (CFP) interferometers for laser ultrasonic measurement systems is the difficulty of controlling the interferometer for optimal performance. In general, for optimal performance, the CFP cavity length must be continuously adjusted to compensate for drift in the laser frequency and changes in the length due to thermal expansion. In some configurations it is also possible to adjust the laser frequency to match a fixed-length cavity to compensate for cavity length changes and laser frequency drift.

SUMMARY OF THE DISCLOSURE

In one embodiment, an interferometer includes a cavity including a pair of mirrors defining a cavity length. A first beam splitter directs an input beam into the cavity through a first phase shift element. A second beam splitter directs a reference beam into the cavity through a second phase shift element.

A first optical detector receives a first and a second output beam from the first beam splitter. The first and the second output beams are generated responsive to the respective input beam and the reference beam. The first optical detector generates a first signal responsive to the first output beam and to the second output beam.

A second optical detector receives a third and a fourth output beam from the second beam splitter. The third and the fourth output beams are generated responsive to the respective input beam and the reference beam. The second optical detector generates a second signal responsive to the third output beam and to the fourth output beam.

A feedback control system receives the first and second signals and in response to at least one of the first and second signals generates a feedback control signal for adjusting the cavity length. The first and second signals are used for ultrasonic measurement of a target.

BRIEF DESCRIPTION OF THE DRAWINGS

For a more complete understanding of the features, example embodiments and possible advantages of the present invention, reference is now made to the detailed description of the invention along with the accompanying figures and in which.

DETAILED DESCRIPTION OF THE INVENTION

Figure 1:
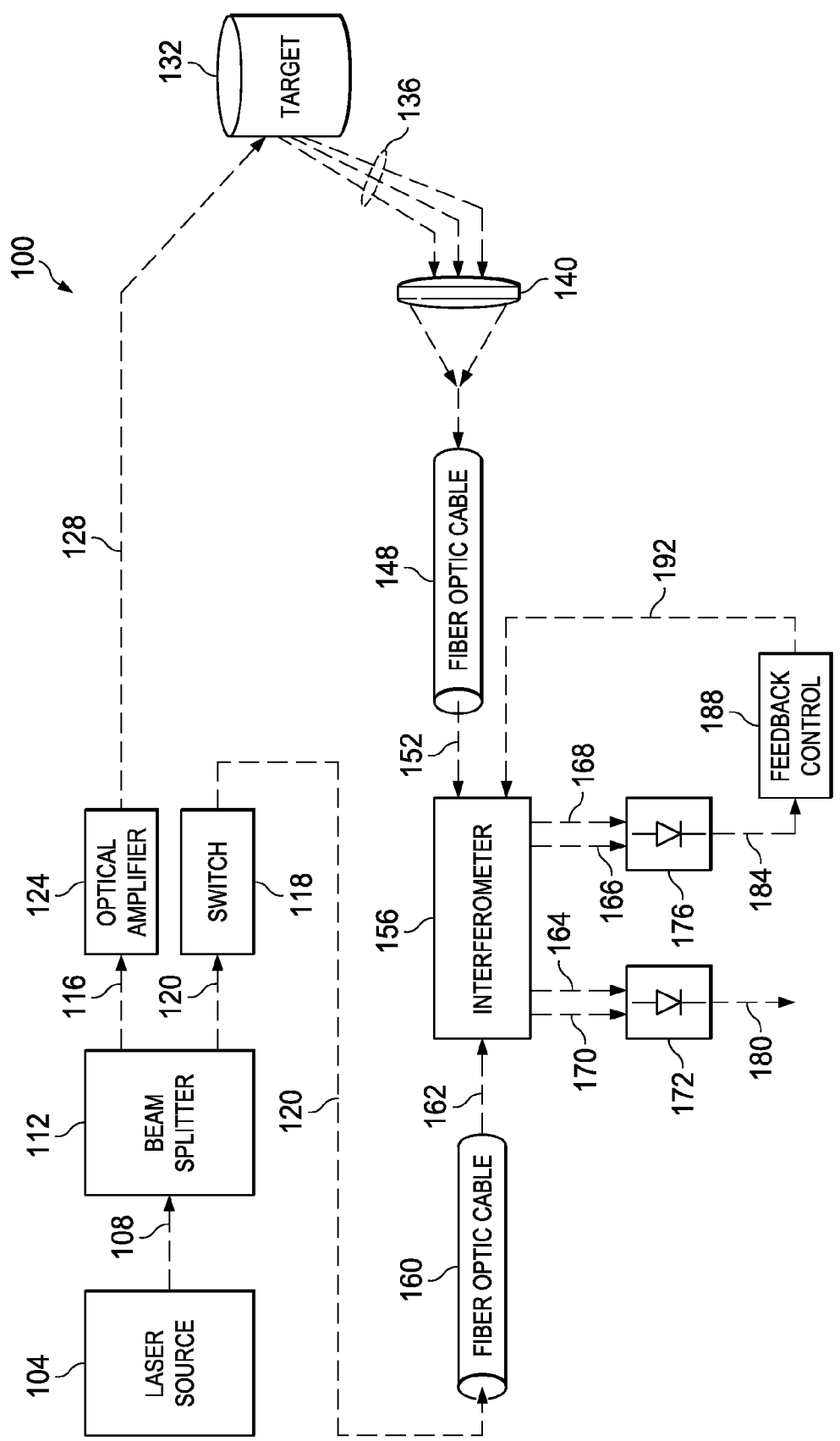
FIG. 1 illustrates a laser ultrasonic measurement system in accordance with an embodiment.

FIG. 1 illustrates a laser ultrasonic measurement system 100 in accordance with an embodiment. The system 100 includes a laser source 104 which generates a source beam 108. A beam splitter 112 splits the source beam 108 into two components: a primary beam 116 and a primary reference beam 120. The primary beam 116 is amplified by an optical amplifier 124, and the amplified beam 128 is directed to a target 132. Scattered beam 136 from the target 132 is accumulated by optical element 140 and directed by a fiber optic cable 148 as an input beam 152 to an interferometer 156.

The primary reference beam 120 is directed by fiber optic cable 160 as reference beam 162 to the interferometer 156. The reference beam 162 counter-propagates within the interferometer 156 with respect to the input beam 152. An optical switch 118 may be used to inhibit the reference beam 162 while the input beam 152 is being fed into the interferometer 156 in order to prevent degradation of the signal to noise ratio (SNR) due to simultaneous input of two beams. If, however, the scattered beam 136 is sufficiently large, the optical switch 118 may not be necessary.

The interferometer 156 generates a first output beam 168 and a second output beam 164 responsive to the input beam 152. Interferometer 156 also generates a first output beam 170 and a second output beam 166 responsive to the reference beam 162. A first optical detector 176 receives the first output beam 168 from input beam 152 and the second output beam 166 from the reference beam 162 and generates a first signal 184, which is used for control of the interferometer 156 or ultrasonic measurement of the target 132.

A second optical detector 172 receives the second output beam 164 from the input beam 152 and the first output beam 170 from the reference beam 162 and in response generates a second signal 180. A feedback control circuit 188 receives the first signal 184, and in response generates a feedback control signal 192, which is used to adjust a cavity length of the interferometer for optimal signal to noise ratio (SNR) performance. In one implementation, the interferometer 156 includes movable mirrors (not shown in FIG. 1) that define its cavity length. The position of the mirrors is adjusted to vary the cavity length responsive to the feedback control signal 192. It should also be appreciated that a similar feedback control signal could be generated from the second detector signal 180 or a combination of signals 184 and 180. Alternatively, feedback control signal 192 could be used to adjust the frequency of source laser 104 for optimal signal to noise ratio (SNR) performance.

In one implementation, the target is subjected to a short pulse laser beam which generates ultrasound waves in the target 132. It will be appreciated that when the target 132 is subjected to a short pulse laser beam, thermal expansion in the target 132 generates ultrasound waves causing a phase shift in the scattered beams 136. The phase shift is transferred to the input beam 152 which is subsequently fed into the interferometer 156. The interferometer 156 demodulates the input beam 152 and generates the output beams 168 and 164 with amplitude modulations representative of the phase shift (i.e., ultrasound waves). Independent of the presence of input beam 152, the signal 184 and the feedback control signal 192 are generated responsive to the characteristic of the source laser 104. It will therefore be appreciated that the reference beam 162 is utilized to adjust the interferometer 156 for optimum SNR performance while the input beam 152 is utilized for the ultrasonic measurement of the target.

Figure 2:
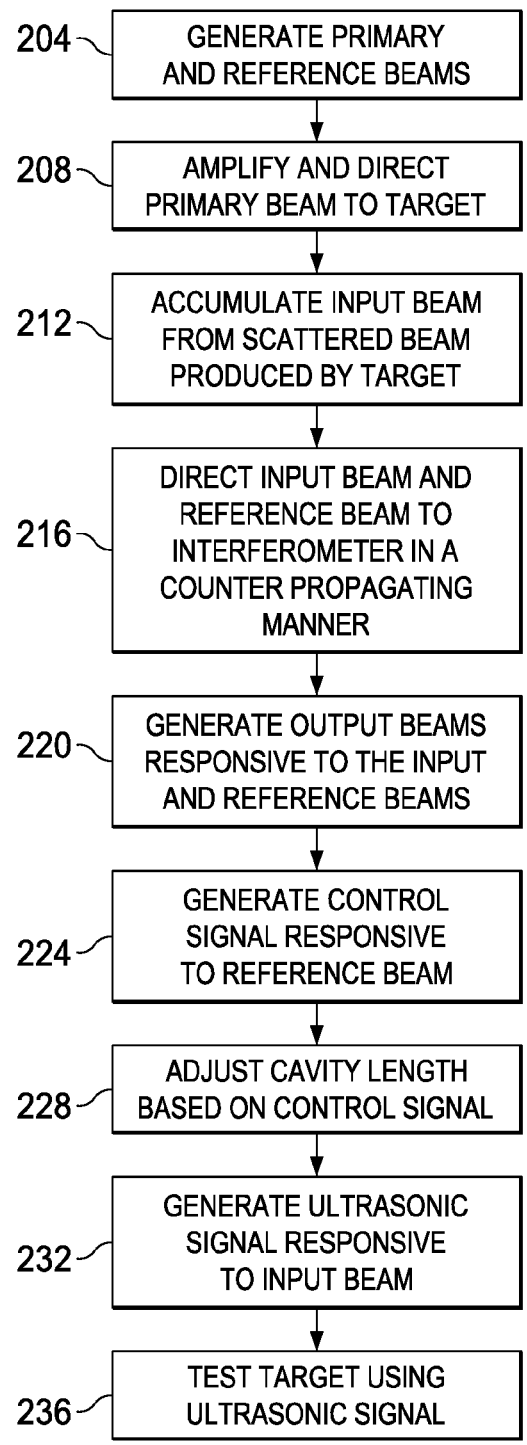
FIG. 2 is a flow diagram of the method steps for adjusting the cavity length of an interferometer.

FIG. 2 is a flow diagram of the method steps for adjusting the cavity length of an interferometer in accordance with one embodiment. In step 204, a primary beam and a reference beam are generated in accordance with the foregoing description. In step 208, the primary beam is amplified and directed to a target. In response, the target produces scattered beams which are accumulated to generate an input beam in step 212.

In step 216, the input beam and the reference beam are directed into the interferometer in a counter-propagating manner. In step 220, output beams are generated responsive to the input beam and the reference beam. In step 224, a control signal is generated responsive to the reference beam. In step 228, the cavity length of the interferometer is adjusted responsive to the control signal. In step 232, ultrasonic signals are generated responsive to the input beam. In step 236, the ultrasonic signal is used for ultrasonic measurement of the target.

Figure 3:
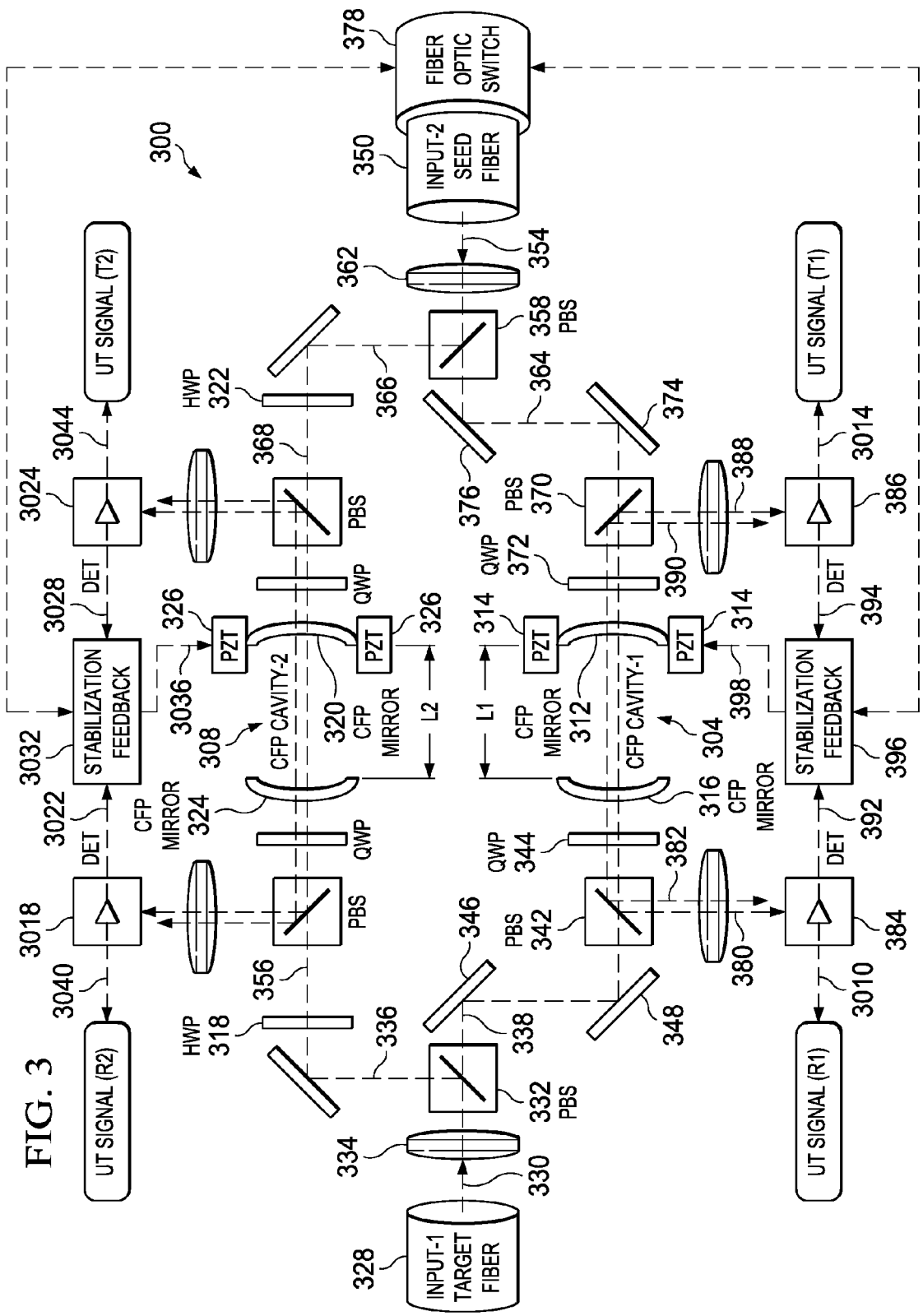
FIG. 3 illustrates an interferometer in accordance with one embodiment.

FIG. 3 illustrates an interferometer 300 in accordance with one embodiment. In one implementation, the interferometer 300 is a confocal Fabry-Perot (CFP) interferometer. The interferometer 300 includes a first and a second cavity 304 and 308, respectively. Although the interferometer 300 has two cavities, 304 and 308, it will be understood by those skilled in the art that the interferometer 300 may be implemented with a single cavity. The first cavity 304 includes a pair of mirrors 312 and 316 defining a first cavity length L1 with at least one movable mirror. Likewise, the second cavity 308 includes a pair of mirrors 320 and 324 defining a second cavity length L2 with at least one movable mirror. The first and second cavity lengths, L1 and L2, are varied by moving the respective mirrors.

A first fiber optic cable 328 directs an input beam 330 to a first beam splitter 332. An optic 334 may be interposed in the path of the input beam 330 to relay the input beam from the first fiber optic cable 328 through the first cavity 304 and the second cavity 308. In one implementation, the first beam splitter 332 may be a polarizing beam splitter (PBS), which splits the input beam 330 into a first polarized input beam 338 (e.g., p-state plane) and a second polarized beam 336 (e.g., s-state plane). The first polarized input beam 338 is directed to a second beam splitter 342, which directs the first polarized input beam 338 into the first cavity 304 through a first phase-shift element 344. In one implementation, the first phase-shift element is a quarter wave plate which applies a quarter-wave phase shift to the first polarized input beam 338 prior to entering the first cavity 304. Mirrors 346 and 348 may be utilized as necessary to direct the first polarized input beam 338 to the second beam splitter 342.

A second fiber optic cable 350 directs a reference beam 354 to a third beam splitter 358. An optic 362 may be interposed in the path of the reference beam 354 to relay the reference beam from the second fiber optic cable 350 through the first cavity 304 and the second cavity 308. In one implementation, the third beam splitter 358 may be a polarizing beam splitter (PBS), which splits the reference beam 354 into a first polarized reference beam 364 (e.g., p-state plane) and a second polarized reference beam 366 (e.g., s-state plane).

The first polarized reference beam 364 is directed to a fourth beam splitter 370, which directs the first polarized reference beam 364 into the first cavity 304 through a second phase-shift element 372. In one implementation, the second phase-shift element 372 is a quarter wave plate which applies a quarter-wave phase shift to the first polarized reference beam 364 prior to entering the first cavity 304. Mirrors 374 and 376 may be utilized as necessary to direct the first polarized reference beam 364 to the fourth beam splitter 370.

An optical switch 378 may be used, if necessary, to inhibit the reference beam 354 while the first input beam 330 is being fed into the first cavity 304 and the second cavity 308 in order to prevent degradation of the signal to noise ratio (SNR) due to simultaneous input of two beams. Depending on the length L1 of the first cavity 304, the first polarized input beam 338 and the first polarized reference beam 364 are each subjected to interference. As a consequence, the second beam splitter 342 directs to a first optical detector circuit 384 a first output beam 380 responsive to the interference of the first polarized input beam 338 and directs a second output beam 382 to the first optical detector circuit 384 responsive to the interference of the first polarized reference beam 364. Likewise, the fourth beam splitter 370 directs to a second optical detector circuit 386 a third output beam 388 responsive to the interference of the first polarized input beam 338 and directs a fourth output beam 390 responsive to the interference of the first polarized reference beam 364. The first optical detector circuit 384 generates a first reference signal 392 responsive to the second output beam 382, and the second optical detector circuit 386 generates a second reference signal 394 responsive to the fourth output beam 390.

Thus, it will be appreciated that the first and second reference signals 392 and 394 are generated responsive to the interference of the first polarized reference beam 364. Accordingly, the first and second reference signals 392 and 394 are representative of the characteristic of the reference beam 354, which is derived from a laser source. A first feedback control circuit 396 receives the first and second reference signals 392 and 394, respectively, and generates a first feedback control signal 398 based on reference signal 392 or reference signal 394, which is used to translate mirror 312 by adjuster 314 to control the first cavity length L1 for optimum SNR performance. Of particular note is the ability to continuously maintain optimum SNR performance exclusively from the reference beam 354 during periods when the input beam 330 is not available.

The first optical detector circuit 384 also generates a first ultrasound signal 3010 responsive to the first polarized input beam 338, and the second optical detector circuit 386 generates a second ultrasound signal 3014 responsive to the first polarized input beam 338. The first and second ultrasound signals 3010 and 3014 are used for ultrasonic measurement of a target (not shown in FIG. 3).

In a similar manner to the description of the operation of the first cavity 304, the second polarized input beam 336 (e.g. s-state) is directed through a third phase-shift element 318 to produce a second polarized input beam 356 (e.g. p-state) and enters the second cavity 308. In a counter direction, the second polarized reference beam 366 (e.g. s-state) is directed through a fourth phase-shift element 322 to produce a second polarized reference beam 368 (e.g. p-state) and enters the second cavity 308. In one implementation, the third and fourth phase-shift elements 318 and 322 are half wave plates which apply a half-wave phase shift to their respective input and reference beams prior to entering the second cavity 308. If the reference beam 354 is polarized, the second fiber optic cable 350 can be rotated to substantially equalize the intensity of the first polarized reference beam 364 and the second polarized reference beam 368. Responsive to the interference of the second polarized reference beam 368 in the second cavity 308, a third optical detector circuit 3018 generates a third reference signal 3022 and a fourth optical detector circuit 3024 generates a fourth reference signal 3028. It will be appreciated that the third and fourth reference signals 3022 and 3028 are representative of the characteristic of the reference beam 354 derived from the laser source (not shown in FIG. 3).

A second feedback control circuit 3032 receives the third and fourth reference signals 3022 and 3028 and in response generates a second feedback control signal 3036 based on reference signal 3022 or 3028, which is used to translate mirror 320 by adjuster 326 in order to control the second cavity length L2.

The third optical detector circuit 3018 also generates a third ultrasound signal 3040 responsive to the second polarized input beam 356, and the fourth optical detector circuit 3024 generates a fourth ultrasound signal 3044 responsive to the second polarized input beam 368. The third and fourth ultrasound signals 3040 and 3044 are used for ultrasonic measurement of the target (not shown in FIG. 3).

It will be apparent to one of skilled in the art that the interferometer 300 can be modified to operate with a single cavity (e.g., cavity 304), instead of two cavities. In a single cavity version, the input beam 330 and the reference beam 354 will be directed into the cavity 304 without first passing through beam splitters 332 and 358, respectively. In a single cavity embodiment, only two optical detector circuits (e.g., 384 and 386) and one feedback control circuit (e.g., 396) are necessary.

It will also be appreciated that one or more of the elements depicted in the drawings/figures can also be implemented in a more separated or integrated manner, or even removed or rendered as inoperable in certain cases, as is useful in accordance with a particular application.

As used in the description herein and throughout the claims that follow, "a," "an" and "the" include plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in the following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed is:

1. An interferometer, comprising:
a first cavity including a pair of mirrors, at least one of which being movable, defining a first cavity length;
a second cavity including a pair of mirrors, at least one of which being movable, defining a second cavity length;
a first beam splitter for directing a first polarized input beam into the first cavity through a first phase shift element;
a second beam splitter for directing a first polarized reference beam into the first cavity through a second phase shift element;
a third beam splitter for directing a second polarized input beam into the second cavity through a third phase shift element;
a fourth beam splitter for directing a second polarized reference beam into the second cavity through a fourth phase shift element;
a first optical detector for receiving from the first beam splitter a first and a second output beam, the first and second output beams being generated responsive to the respective first polarized input beam and the first polarized reference beam, the first optical detector generating a first signal responsive to the first output beam and to the second output beam;
a second optical detector for receiving from the second beam splitter a third and a fourth output beam, the third and fourth output beams being generated responsive to the respective first polarized input beam and the first polarized reference beam, the second optical detector generating a second signal responsive to the third output beam and the fourth output beam;
a third optical detector for receiving from the third beam splitter a fifth and a sixth output beam, the fifth and sixth output beams being generated responsive to the respective second polarized input beam and the second polarized reference beam, the third optical detector generating a third signal responsive to the fifth output beam and to the sixth output beam;
a fourth optical detector for receiving from the fourth beam splitter a seventh and an eighth output beam, the seventh and eighth output beams being generated responsive to the respective second polarized input beam and the second polarized reference beam, the fourth optical detector generating a fourth signal responsive to the seventh output beam and to the eighth output beam;
a first feedback control system for receiving the first and second signals and in response to at least one of the first and second signals generating a first feedback control signal for adjusting the first cavity length; and
a second feedback control system for receiving the third and fourth signals and in response to at least one of the third and fourth signals generating a second feedback control signal for adjusting the second cavity length.

2. The interferometer of claim 1, wherein the first feedback control system generates the first feedback control signal responsive to the first and second signals.

3. The interferometer of claim 1, wherein the second feedback control system generates the second feedback control signal responsive to the third and fourth signals.

4. The interferometer of claim 1, wherein the first and second polarized input beams are generated from an input beam, and wherein the input beam is generated from scattered beams.

5. The interferometer of claim 1, wherein the first and second polarized reference beams are generated from a reference beam.

6. The interferometer of claim 4, wherein a laser source generates a source beam which is split into a reference beam and a primary beam, wherein the primary beam is applied to a target which generates the scattered beams.

7. The interferometer of claim 4, wherein a laser source generates a source beam which is split into a reference beam and a primary beam, wherein the primary beam is amplified and applied to a target which generates the scattered beams.

8. The interferometer of claim 1, wherein the beam splitter element is a polarizing beam splitter.

9. The interferometer of claim 1, wherein the phase-shift element is a quarter wave plate.

10. The interferometer of claim 1, wherein the first and the second cavity lengths are adjusted by moving the respective mirrors.

11. The interferometer of claim 1, wherein the signals are generated responsive to ultrasound was in the target.

12. The interferometer of claim 1, wherein the signals are representative of ultrasound waves in the target.

13. The interferometer of claim 1, wherein the signals are representative of the frequency of the reference beam.

14. The interferometer of claim 1, wherein the reference beam can be attenuated when the signals are representative of the input beam.

15. An interferometer, comprising:
a cavity including a pair of mirrors defining a cavity length;
a first beam splitter for directing an input beam into the cavity through a first phase shift element;
a second beam splitter for directing a reference beam into the cavity through a second phase shift element;
a first optical detector for receiving from the first beam splitter a first and a second output beam, the first and the second output beam being generated responsive to the respective input beam and the reference beam, the first optical detector generating a first signal responsive to the first output beam and to the second output beam;
a second optical detector for receiving from the second beam splitter a third and a fourth output beam, the third and the fourth output beam being generated responsive to the respective input beam and the reference beam, the second optical detector generating a second signal responsive to the third output beam and to the fourth output beam; and
a feedback control system for receiving the first and second signals and in response to at least one of the first and second signals generating a feedback control signal for adjusting the cavity length.

16. The interferometer of claim 15, further comprising adjusting the frequency of a laser source in response to the feedback control signal.

17. The interferometer of claim 15, wherein the feedback control system generates the feedback control signal responsive to the first and second signals.

18. The interferometer of claim 15, wherein the first and second signals are used for ultrasonic measurement of a target.

19. The interferometer of claim 15, wherein the input beam is formed from scattered beams off a target.

20. The interferometer of claim 19, wherein a laser source generates a source beam which is split into the reference beam and a primary beam, wherein the primary beam is applied to a target which generates the scattered beams.

21. The interferometer of claim 19, wherein a laser source generates a source beam which is split into the reference beam and a primary beam, wherein the primary beam is amplified and applied to a target which generates the scattered beams.

22. The interferometer of claim 15, further comprising a first optic for directing the input beam to the first beam splitter and a second optic for directing the reference beam to the second beam splitter.

23. The interferometer of claim 15, wherein the first and second beam splitter elements are polarizing beam splitters.

24. The interferometer of claim 15, wherein the first and second phase-shift elements are quarter wave plates.

25. The interferometer of claim 15, wherein the cavity length is adjusted by moving the mirrors.

26. The interferometer of claim 15, wherein the input beam is phase shifted by an ultrasound wave generated in the target.

27. The interferometer of claim 15 wherein the ultrasound signal is representative of ultrasonic waves in the target.

28. A method for adjusting a cavity length of an interferometer having at least one movable mirror, comprising:
generating a reference beam and a primary beam;
directing the primary beam onto a target;
accumulating scattered beam from the target and generating an input beam responsive to the scattered beam;
directing the input beam and the reference beam into the interferometer through different beam splitters;
generating a first output beam responsive to the input beam and a second output beam responsive to the reference beam;
generating a control signal responsive to the second output beam and an ultrasound signal responsive to the first output beam; and
adjusting the cavity length of the interferometer responsive to the control signal.

29. The method of claim 28, wherein the reference beam and the primary beam are generated from a source beam.

30. The method of claim 28, wherein the reference beam and the primary beam are generated from a source beam and the primary beam is amplified before directed onto a target.

31. The method of claim 28, wherein the input beam is accumulated and generated from the scattered beam by an optic.

32. The method of claim 28, further comprising adjusting the cavity length of the interferometer to optimize the signal to noise ratio (SNR) of the interferometer.

33. A method for adjusting the frequency of a source beam relative to an interferometer cavity, comprising:
generating a reference beam and a primary beam derived from the source beam;
directing the primary beam onto a target;
accumulating scattered beam from the target and generating an input beam responsive to the scattered beam;
directing the input beam and the reference beam into the interferometer cavity through different polarizing beam splitters;
generating a first output beam responsive to the input beam and a second output beam responsive to the reference beam;

generating a control signal responsive to the second output beam; and adjusting the frequency of the source beam responsive to the control signal.

34. The method of claim 33, wherein the reference beam and the primary beam are generated from a source beam.

35. The method of claim 33, wherein the reference beam and the primary beam are generated from a source beam and the primary beam is amplified before directed onto a target.

36. The method of claim 33, wherein the input beam is accumulated and generated from the scattered beam by an optic.

37. The method of claim 33, further comprising adjusting the laser frequency to optimize the signal to noise ratio (SNR) of the interferometer.

* * * * *